(12) United States Patent
Coillard

(10) Patent No.: US 7,059,121 B2
(45) Date of Patent: Jun. 13, 2006

(54) SYSTEM FOR PROVIDING ASSISTANCE IN REGENERATING A NOX TRAP

(75) Inventor: Véronique Coillard, Carrieres sur Seine (FR)

(73) Assignee: Peugeot Citron Automobiles SA, Velizy-Villacoublay (FR)

( * ) Notice: Subject to any disclaimer, the term of this patent is extended or adjusted under 35 U.S.C. 154(b) by 151 days.

(21) Appl. No.: 10/831,202

(22) Filed: Apr. 26, 2004

(65) Prior Publication Data
US 2004/0226281 A1 Nov. 18, 2004

(30) Foreign Application Priority Data
May 12, 2003 (FR) .................................. 03 05695

(51) Int. Cl.
*F01N 3/00* (2006.01)
(52) U.S. Cl. .......................................... 60/295; 60/285
(58) Field of Classification Search .................. 60/285, 60/295
See application file for complete search history.

(56) References Cited

U.S. PATENT DOCUMENTS 4,362,605 A * 12/1982 Bozon et al. ............... 205/784

FOREIGN PATENT DOCUMENTS

| DE | 198 27 469 | 1/1999 |
|----|------------|--------|
| EP | 0 814 248 | 12/1997 |
| WO | WO 00/71870 | 11/2000 |
| WO | WO 01/53672 | 7/2001 |

* cited by examiner

*Primary Examiner*—Thomas Denion
*Assistant Examiner*—Marc I. Nagy
(74) *Attorney, Agent, or Firm*—Nicolas E. Seckel

(57) ABSTRACT

A system for providing assistance in regenerating a storage/destorage NOx trap integrated in an exhaust system of a motor vehicle engine, comprising means for controlling the operation of means for injecting fuel into the cylinders of the engine to cause the engine to switch from a standard mode of operation during which NOx is stored in the trap to a regeneration mode in which NOx is destored from the trap and the trap is regenerated, the system including two λ probes placed at equal distances from the NOx trap downstream therefrom in the exhaust system, the outputs from the probes being connected to differential measurement means for measuring the output signals from the probes in order to determine the quantity of NOx in the exhaust gas so as to cause the control means to trigger a stage of regenerating the trap when the measurement exceeds a predetermined threshold.

1 Claim, 1 Drawing Sheet

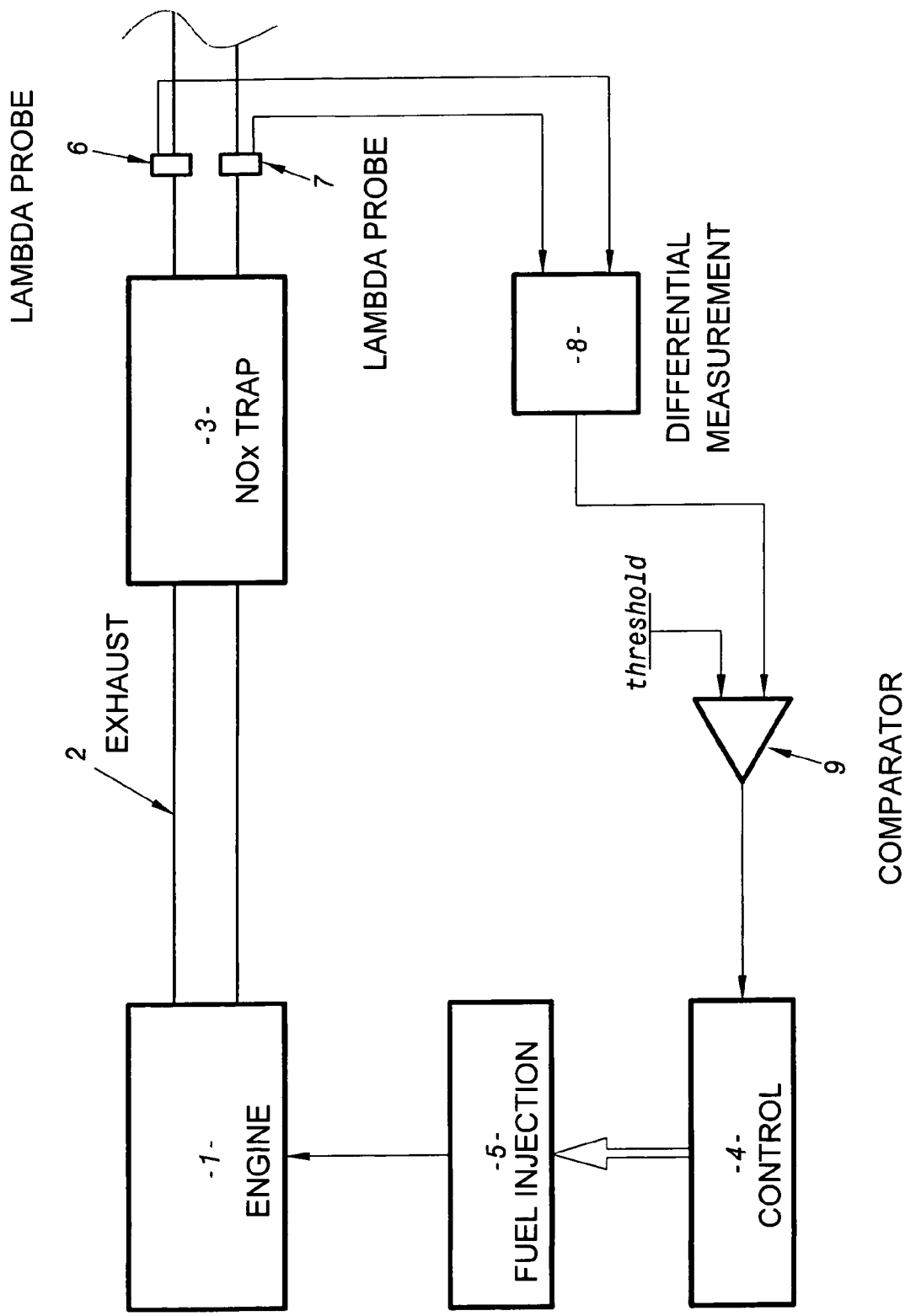

SYSTEM FOR PROVIDING ASSISTANCE IN REGENERATING A NOX TRAP

The present invention relates to a system for providing assistance in regenerating a storage/destorage NOx trap integrated in an exhaust system of a motor vehicle engine.

BACKGROUND OF THE INVENTION

Reducing NOx emissions by DeNOx catalysis with storage/destorage constitutes one of the technical solutions for satisfying standards relating to this type of exhaust, in particular, the EURO IV standards.

To this end, use of a NOx trap, constituted of barium sulfate, for example, has been envisaged for absorbing NOx during standard operation of the engine.

When the trap becomes saturated, it is proposed to trigger a transient destorage stage by causing the engine to switch temporarily from its standard operating mode with a lean mixture to operating in a regeneration mode using a rich mixture. This produces reducing agents, such as HC and CO, for example, that enable the NOx to be reduced, which is then desorbed from the trap, as in a traditional catalytic unit.

For this purpose, such a system for providing assistance in regeneration includes means for controlling the operation of means for injecting fuel into the cylinders of the engine in order to cause the engine to switch from a standard mode of operation with a lean mixture to a regeneration mode of operation with a rich mixture.

One of the ways of knowing when the NOx trap is in a saturated state is to use a NOx sensor in the exhaust system.

However, present NOx sensors are unreliable and relatively expensive.

OBJECT AND SUMMARY OF THE INVENTION

The object of the invention is thus to solve these problems.

To this end, the invention provides a system for providing assistance in regenerating a storage/destorage NOx trap integrated in an exhaust system of a motor vehicle engine, the system comprising means for controlling the operation of means for injecting fuel into the cylinders of the engine to cause the engine to switch from a standard mode of operation with a lean mixture during which NOx is stored in the trap to a regeneration mode with a rich mixture in which NOx is destored from the trap and the trap is regenerated, the system including two $\lambda$ probes placed at equal distances from the NOx trap downstream therefrom in the exhaust system, one of the $\lambda$ probes including a rhodium-based catalytic layer, the outputs from the probes being connected to differential measurement means for measuring the output signals from the probes in order to determine the quantity of NOx in the exhaust gas so as to cause the control means to trigger a stage of regenerating the trap when the measurement exceeds a predetermined threshold.

BRIEF DESCRIPTION OF THE DRAWING

The invention will be better understood on reading the following description given purely by way of example and made with reference to the accompanying drawing which is a block diagram showing the general structure and the operation of a system of the invention for providing assistance in regeneration.

MORE DETAILED DESCRIPTION

The FIGURE shows a system for providing assistance in regenerating a storage/destorage NOx trap integrated in an exhaust system of a motor vehicle engine.

In the FIGURE, the engine is designated by overall reference 1, the exhaust system is designated by overall reference 2, and the NOx trap is designated by overall reference 3.

The system comprises means 4 for controlling the operation of the means 5 for injecting fuel into the cylinders of the engine, to switch the engine from a standard mode of operation with a lean mixture during which NOx is stored in the trap, to a regeneration mode of operation with a rich mixture in which NOx is destored from the trap and the trap is regenerated in conventional manner.

According to the invention, the system further comprises two $\lambda$ probes designated by general references 6 and 7 in the FIGURE, the probes being placed at equal distances from the NOx trap 3, downstream therefrom in the exhaust system, one of the probes having a rhodium-based catalytic layer so as to react to the presence of NOx in the exhaust gas.

The outputs from the probes are connected to means for differentially measuring the signals they output in order to determine the quantity of NOx in the exhaust gas.

These differential measurement means are given overall reference 8 and present an output which is connected to comparator means 9 for comparing the differential measurement with a predetermined threshold value so that when the differential measurement reaches the predetermined threshold, the control means 4 are caused to trigger operation in trap regeneration mode.

$\lambda$ probes are well known in the state of the art and have been in regular use, for example with gasoline engines.

In general, they are inactive relative to NOx, insofar as platinum and/or palladium electrodes are not active relative to NOx. However, some suppliers offer $\lambda$ probes fitted with a rhodium-based catalytic layer (platinum-rhodium), which therefore present catalytic activity relative to NOx.

It is then possible by associating these two types of $\lambda$ probes to create a differential measurement circuit for obtaining the quantity of NOx in the output from the trap. If this quantity of NOx exceeds the determined threshold, the trap is saturated and needs to be regenerated.

It is then regenerated in conventional manner by suitable control of the engine so as to cause it to switch to a rich-mixture regeneration mode.

It will thus be understood that this structure presents certain advantages, in particular, in terms of cost, simplicity, and reliability.

Naturally, the invention is applicable to any type of heat engine, and in particular gasoline or diesel engines.

What is claimed is:

1. A system for providing assistance in regenerating a storage/destorage NOx trap integrated in an exhaust system of a motor vehicle engine, the system comprising:

means for controlling the operation of means for injecting fuel into the cylinders of the engine to cause the engine to switch from a standard mode of operation with a lean mixture during which NOx is stored in the trap to a regeneration mode with a rich mixture in which NOx is destored from the trap and the trap is regenerated, wherein the system further comprises two $\lambda$ probes placed at equal distances from the NOx trap downstream therefrom in the exhaust system, one of the $\lambda$ probes including a rhodium-based catalytic layer, the outputs from the probes being connected to differential measurement means for measuring the output signals from the probes in order to determine the quantity of NOx in the exhaust gas so as to cause the control means to trigger a stage of regenerating the trap when the measurement exceeds a predetermined threshold.

* * * * *